United States Patent
Porter

(10) Patent No.: US 11,039,691 B2
(45) Date of Patent: Jun. 22, 2021

(54) THERAPEUTIC TRAVEL AND SPA PILLOW

(71) Applicant: Selena Porter, Las Vegas, NV (US)

(72) Inventor: Selena Porter, Las Vegas, NV (US)

( * ) Notice: Subject to any disclaimer, the term of this patent is extended or adjusted under 35 U.S.C. 154(b) by 46 days.

(21) Appl. No.: 16/530,870

(22) Filed: Aug. 2, 2019

(65) Prior Publication Data
US 2021/0030160 A1 Feb. 4, 2021

(51) Int. Cl.
| A47G 9/10 | (2006.01) |
| A61F 9/04 | (2006.01) |
| A47C 16/00 | (2006.01) |
| A47G 9/00 | (2006.01) |
| A61F 7/02 | (2006.01) |
| A61F 7/00 | (2006.01) |

(52) U.S. Cl.
CPC .............. *A47C 16/00* (2013.01); *A47G 9/007* (2013.01); *A47G 9/1045* (2013.01); *A47G 9/1081* (2013.01); *A61F 7/02* (2013.01); *A61F 9/04* (2013.01); *A47G 2009/1018* (2013.01); *A61F 7/007* (2013.01); *A61F 2007/0004* (2013.01)

(58) Field of Classification Search
CPC ...... A47C 16/00; A47G 9/1045; A47G 9/007; A47G 9/1081; A47G 2009/1018; A61F 7/02; A61F 9/04; A61F 2007/0004; A61F 7/007

See application file for complete search history.

(56) References Cited

U.S. PATENT DOCUMENTS

| 4,679,263 | A | * | 7/1987 | Honer | A47C 7/383 297/393 |
| 5,881,390 | A | * | 3/1999 | Young | A41D 20/00 2/209.13 |
| 6,088,836 | A | * | 7/2000 | de Cordova | A47C 7/383 2/15 |
| 6,345,401 | B1 | * | 2/2002 | Frydman | A47G 9/10 5/636 |
| 6,381,760 | B1 | * | 5/2002 | Lampe | A42B 3/00 2/414 |
| 6,625,820 | B1 | * | 9/2003 | Lampe | A42B 3/00 2/171 |
| 9,138,086 | B1 | * | 9/2015 | Bamberg | A47C 7/383 |
| D853,752 | S | * | 7/2019 | Porter | D6/601 |
| 2008/0216244 | A1 | * | 9/2008 | Minton | A47G 9/10 5/640 |
| 2012/0210516 | A1 | * | 8/2012 | Popovic | A47G 9/1081 5/640 |
| 2013/0312192 | A1 | * | 11/2013 | Lee | A47G 9/007 5/639 |

(Continued)

*Primary Examiner* — Eric J Kurilla

(57) ABSTRACT

A therapeutic travel and spa pillow that can be used during travel for therapeutic purposes. In further detail, the therapeutic travel and spa pillow can be worn when riding in a transport vehicle such as, but not limited to, a train, bus, car, or plane in order to receive therapeutic benefits. The therapeutic travel and spa pillow includes a pillow body, a left strap, and a right strap. The pillow body is a cushioned support for the head and shoulders of the user. The left strap and the right strap allow the user to secure the therapeutic travel and spa pillow underneath his or her chin. This prevents the therapeutic travel and spa pillow from falling of the shoulders of the user. The left strap and the right strap are preferably cord-like strips of material.

10 Claims, 10 Drawing Sheets

(56) References Cited

U.S. PATENT DOCUMENTS

| | | | |
|---|---|---|---|
| 2014/0345055 A1* | 11/2014 | Li | A47G 9/1027 5/630 |
| 2016/0000607 A1* | 1/2016 | Bamberg | A47G 9/0253 2/15 |
| 2016/0120253 A1* | 5/2016 | Schenk | A47C 7/383 2/173 |
| 2019/0045952 A1* | 2/2019 | Porter | A47G 9/007 |
| 2019/0208936 A1* | 7/2019 | Thomas | A47G 9/066 |

* cited by examiner

THERAPEUTIC TRAVEL AND SPA PILLOW

FIELD OF THE INVENTION

The present invention relates generally to pillows. More specifically, the present invention is a pillow that can be used during travel for therapeutic purposes.

BACKGROUND OF THE INVENTION

Travel is very common in the present day. There are various forms of transportation for travel including, but not limited to, travel by plane, train, or car. When traveling for long periods of time in these forms of transportation, an individual may get tired and fall asleep. Further, an individual may grow discomfort for being seated for a long time. In order to experience a more comfortable travel experience, travel pillows may be used. Travel pillows provide support to the head, neck and lumbar area of an individual which allows said individual to sleep or generally be more comfortable during travel. However, conventional travel pillows are generally used for support of the head, neck, and lumbar area. Certain individuals may require or want a pillow that can provide therapy while also supporting the head, neck, and lumbar area. There is a need for a pillow that can be used during travel for therapeutic purposes.

It is therefore the objective of the present invention to provide a therapeutic travel and spa pillow. The present invention includes pockets which are able to hold therapeutic devices such as, but not limited to, cooling or heating devices. Further, the present invention includes fillings which provide comfort and support. More specifically, one of the fillings is able to store heat which allows the present invention to be heated in order to provide a heated therapeutic effect. Moreover, the present invention includes an eye covering feature which allows a user to cover his or her eyes while using the present invention.

DETAIL DESCRIPTIONS OF THE INVENTION

All illustrations of the drawings are for the purpose of describing selected versions of the present invention and are not intended to limit the scope of the present invention.

In reference to FIGS. 1 through 8, the present invention is a travel spa pillow that can be used during travel for therapeutic purposes. In further detail, the present invention can be worn when riding in a transport vehicle such as, but not limited to, a train, bus, car, or plane in order to receive therapeutic benefits. The present invention comprises a pillow body 1, a left strap 2, and a right strap 3. The pillow body 1 is a cushioned support for the head of the user. The pillow body 1 may be composed of any material and can be any size. The pillow body 1, when the present invention is worn, covers the back and the sides of the head of the user while resting on the shoulders of the user. The left strap 2 and the right strap 3 allow the user to secure the present invention underneath his or her chin. This prevents the present invention from falling of the shoulders of the user. The left strap 2 and the right strap 3 are preferably cord-like strips of material.

Figure 1:
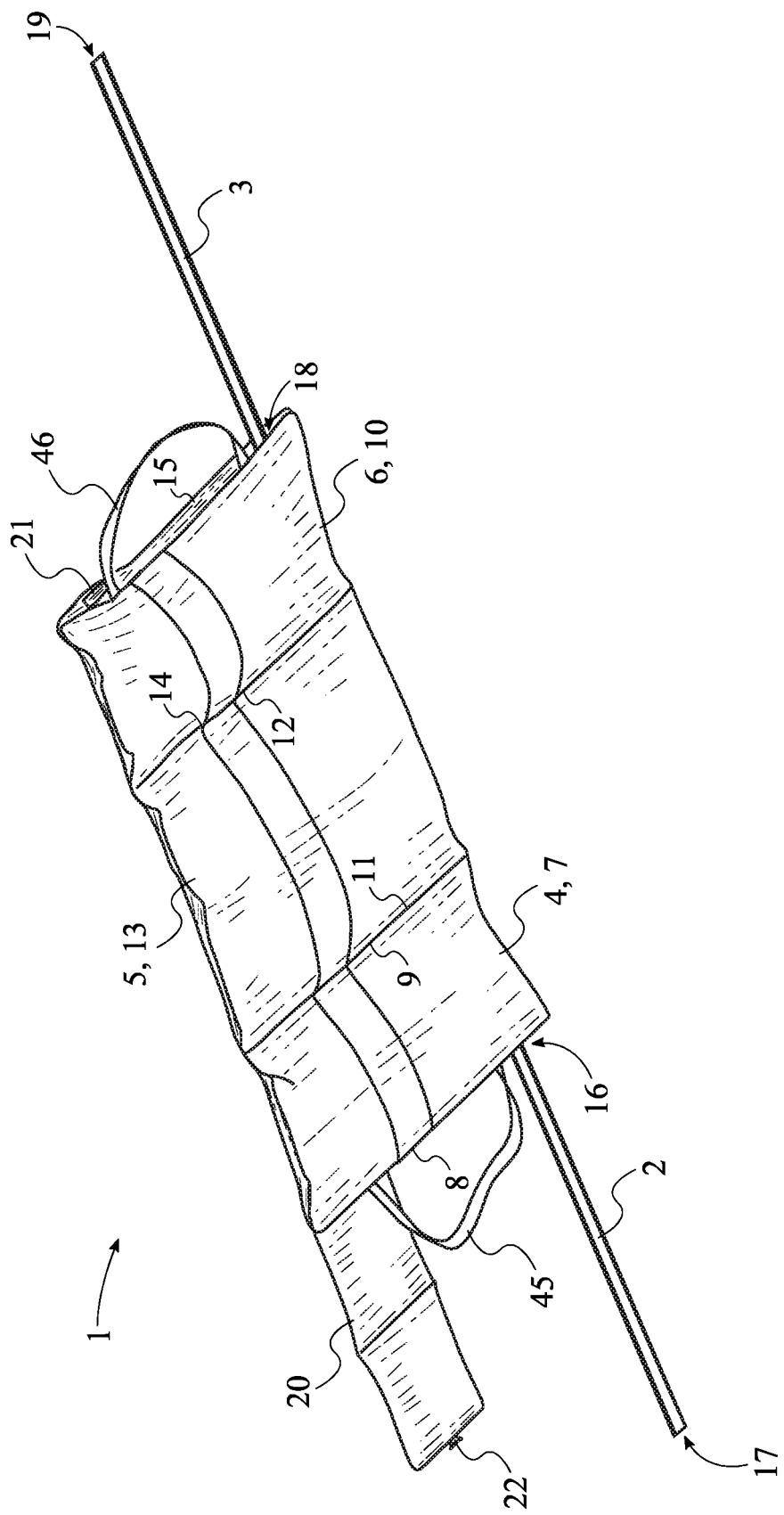
FIG. 1 is a front perspective view of the present invention in the open configuration.
Figure 2:
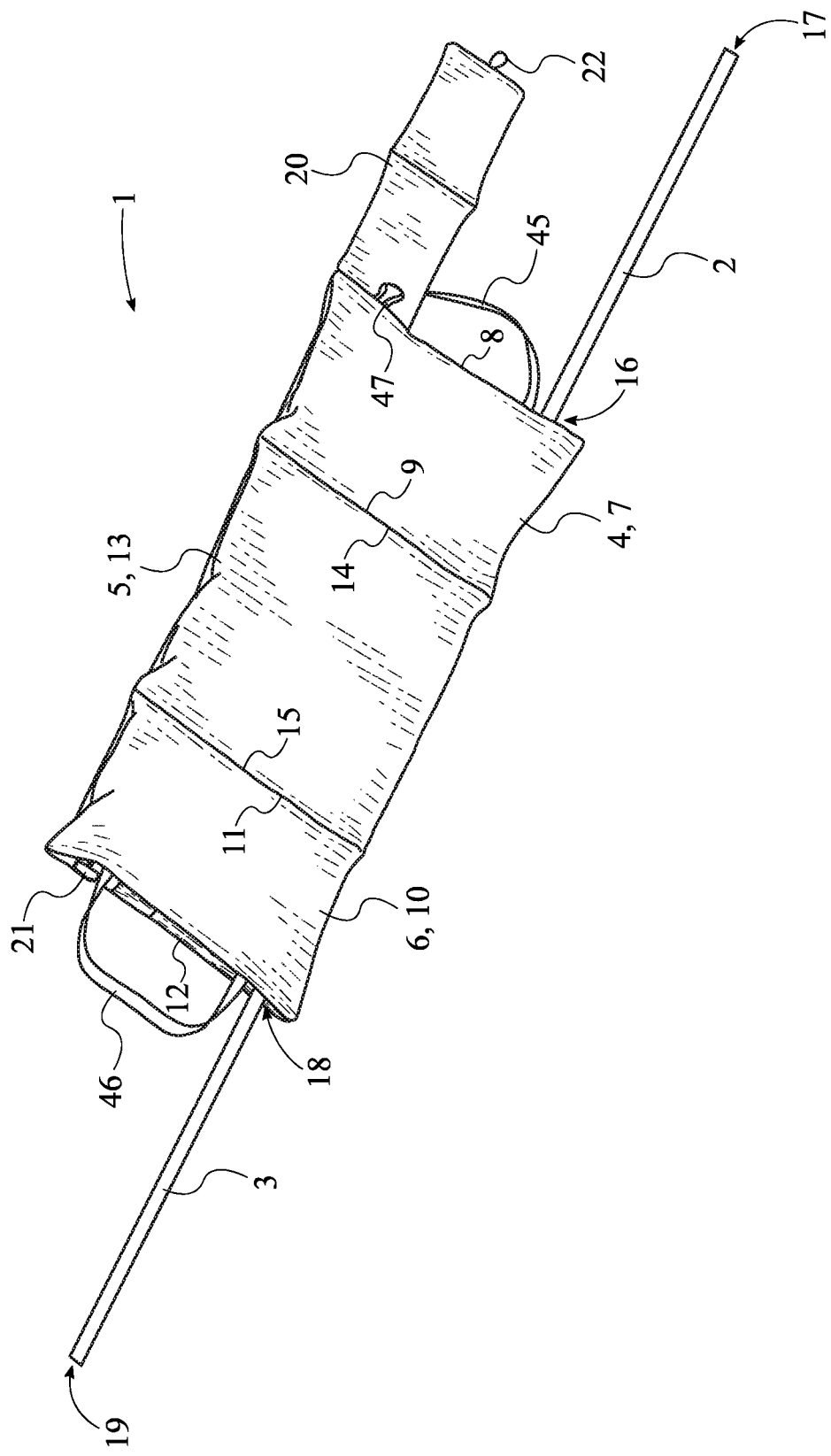
FIG. 2 is a rear perspective view of the present invention in the open configuration.

The general configuration of the aforementioned components allows the present invention to be worn by the user during travel for therapeutic purposes. Further, the present invention is able to be stored and transported easily due to the configuration of the aforementioned components. With reference to FIGS. 1 and 2, the pillow body 1 comprises a left section 4, a middle section 5, and a right section 6. The left section 4, middle section 5, and right section 6 are foldable parts of the pillow body 1. This allows the pillow body 1 to be folded around the head of the user. The left section 4, the middle section 5, and the right section 6 each comprises a section body 7, 10, 13, a first edge 8, 11, 14, and a second edge 9, 12, 15. The left strap 2 and the right strap 3 each comprises a fixed end 16, 18 and a free end 17, 19. The first edge 8, 11, 14 and the second edge 9, 12, 15 are positioned parallel and opposite to each other across the section body 7, 10, 13. The second edge 9 of the left section 4 is foldably connected along the first edge 14 of the middle section 5. This arrangement allows the left section 4 to be folded toward the middle section 5. Further, the second edge 15 of the middle section 5 is foldably connected along the first edge 11 of the right section 6. This arrangement allows the right section 6 to be folded toward the middle section 5. In further detail, the left section 4 and the right section 6 can be folded towards the middle section 5 to contact the sides of the head of the user while the middle section 5 contacts the back of the head of the user. The fixed end 16 of the left strap 2 is connected adjacent to the first edge 8 of the left section 4. This arrangement properly connects the left strap 2 to the pillow body 1 in order to be easily accessed by the user. Similarly, the fixed end 18 of the right strap 3 is connected adjacent to the second edge 12 of the right section 6. This arrangement properly connects the right strap 3 to the pillow body 1 in order to be easily accessed by the user.

With reference to FIGS. 1 through 4, the present invention can be arranged into an open configuration to support the lower back and lumbar area of the user. Also, the present invention can be arranged into the open configuration when not being worn by the user. The first edge 8 of the left section 4 is positioned offset from the second edge 12 of the right section 6. This arrangement allows the pillow body 1 to be in a flat state. In further detail, the left section 4 is not folded towards the middle section 5 and the right section 6 is not folded towards the middle section 5. Further, the open configuration allows the present invention to be easily stored for travel.

Figure 5:
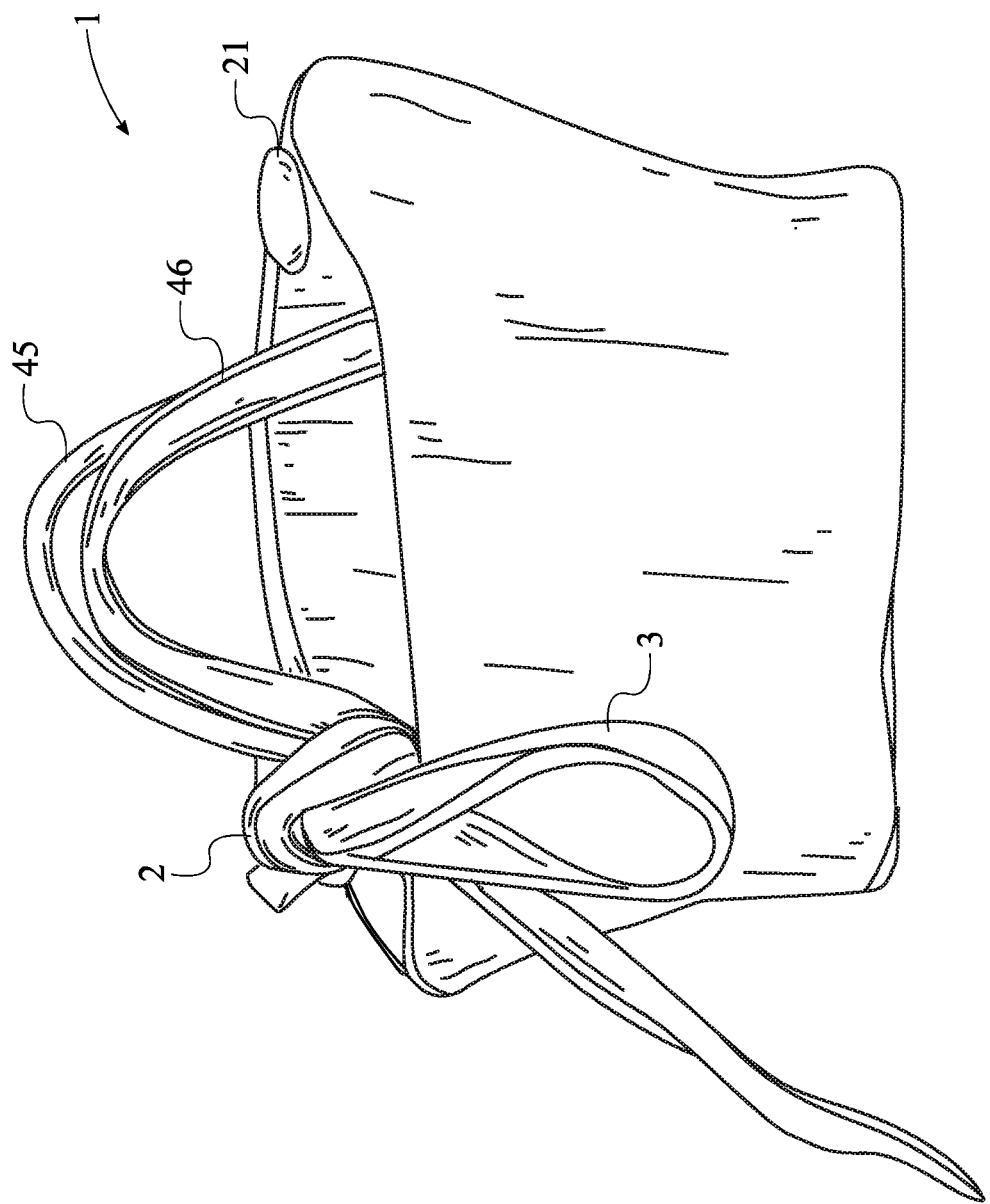
FIG. 5 is a side perspective view of the present invention in the closed configuration.
Figure 6:
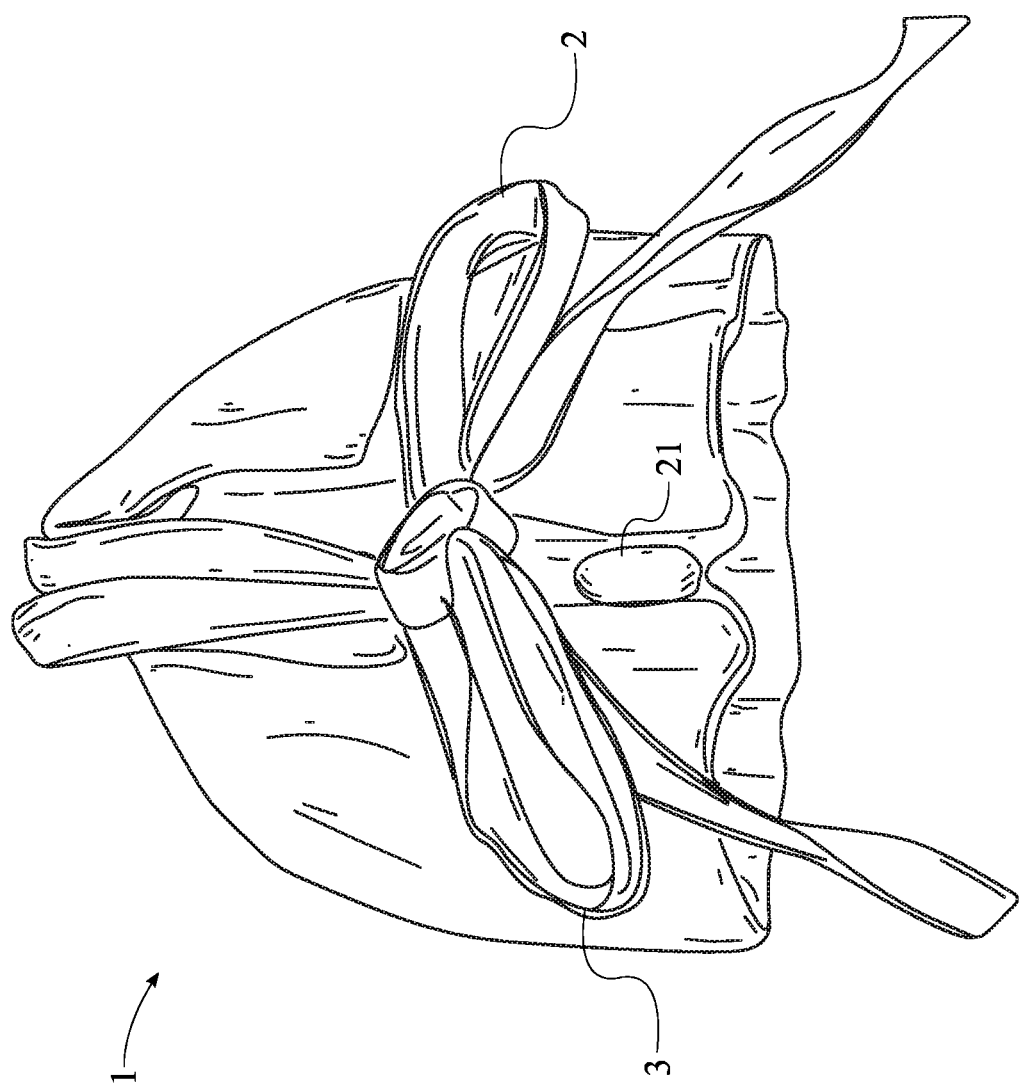
FIG. 6 is a top perspective view of the present invention in the closed configuration.

With reference to FIGS. 5 and 6, the pillow body 1 can be arranged in a closed configuration. The first edge 8 of the left section 4 is positioned adjacent to the second edge 12 of the right section 6. In further detail, the left section 4 and the right section 6 are folded towards the middle section 5 and therefore the left section 4 contacts the right section 6. Further, this arrangement allows the pillow body 1 to fully cover the head of the user. The free end 17 of the left strap 2 is attached to the free end 19 of the right strap 3. This arrangement is used to secure the present invention underneath the chin of the user. In further detail, the free end 17 of the left strap 2 is preferably tied to the free end 19 of the right strap 3, but the free end 17 of the left strap 2 can be attached to the free end 19 of the right strap 3 through any fastening means such as, but not limited to, a clip buckle fastener or a hook-and-loop fastener. The closed configuration is used when the present invention is worn by the user or to transport the present invention when not stored inside a suitcase or similar storage device.

Figure 3:
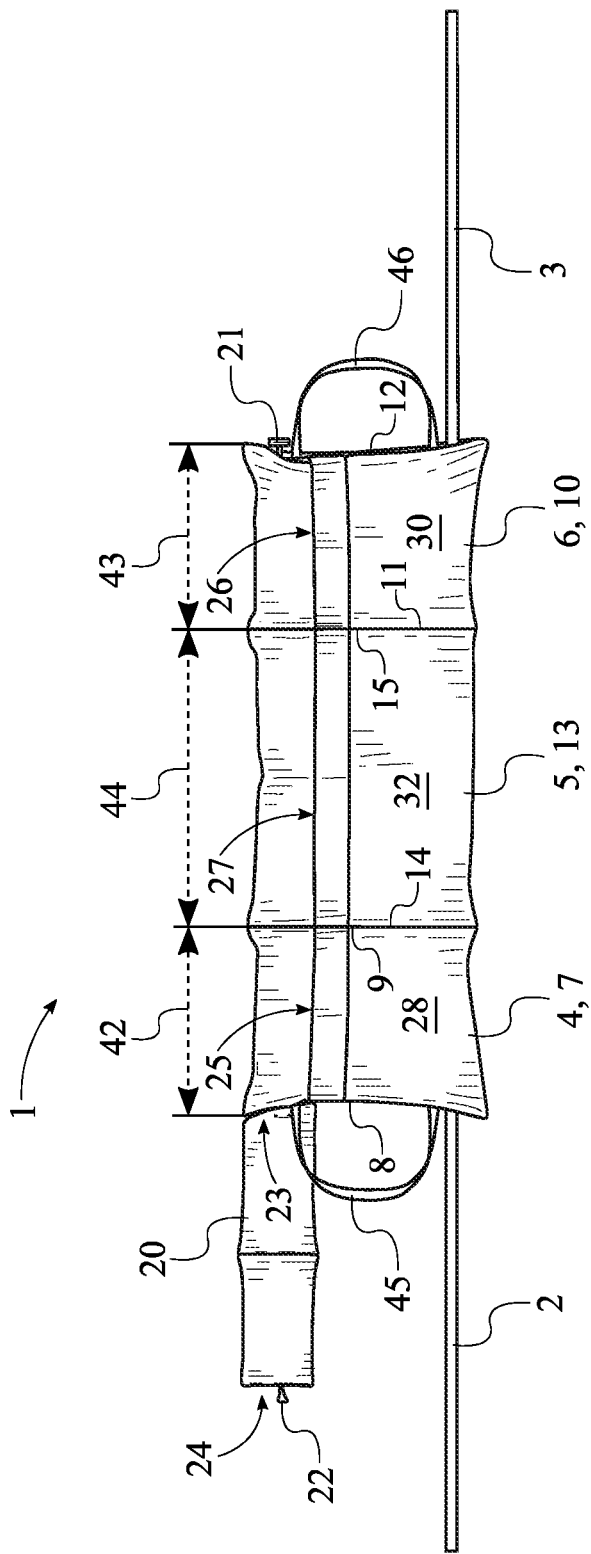
FIG. 3 is a front view of the present invention in the open configuration.

With reference to FIGS. 1 and 3, the present invention may further comprise an eye-mask 20, an eye-mask hook 21, and an eye-mask loop 22. The eye-mask 20 is a weighted and cushioned eye mask that is used to cover the eyes of the user. The eye-mask 20 is preferably filled with flax seeds or other similar material that can be used to add weight and heat conduction. The eye-mask 20 may be composed of any material. The eye-mask hook 21 is used to receive the eye-mask loop 22 in order to fully secure the eye-mask 20 to the pillow body 1. The eye-mask loop 22 is used to attach the eye-mask 20 to the eye-mask hook 21. The eye-mask 20 comprises a first mask end 23 and a second mask end 24. The first mask end 23 is hingedly connected to the first edge 8 of the left section 4 and is positioned offset from the fixed end 16 of the left strap 2. This arrangement allows the eye-mask 20 to be freely rotated about the first edge 8 of the left section 4. The eye-mask loop 22 is connected adjacent to the second mask end 24. This arrangement allows the user to access the eye-mask loop 22 in order to engage the eye-mask loop 22 to the eye-mask hook 21. The eye-mask hook 21 is connected onto the second edge 12 of the right section 6. This arrangement allow the user to fully secure the eye-mask 20 to the pillow body 1. When in the closed configuration, the eye-mask loop 22 is engaged to the eye-mask hook 21 for the eye-mask 20 to cover the eyes of the user when the present invention is worn.

Figure 7:
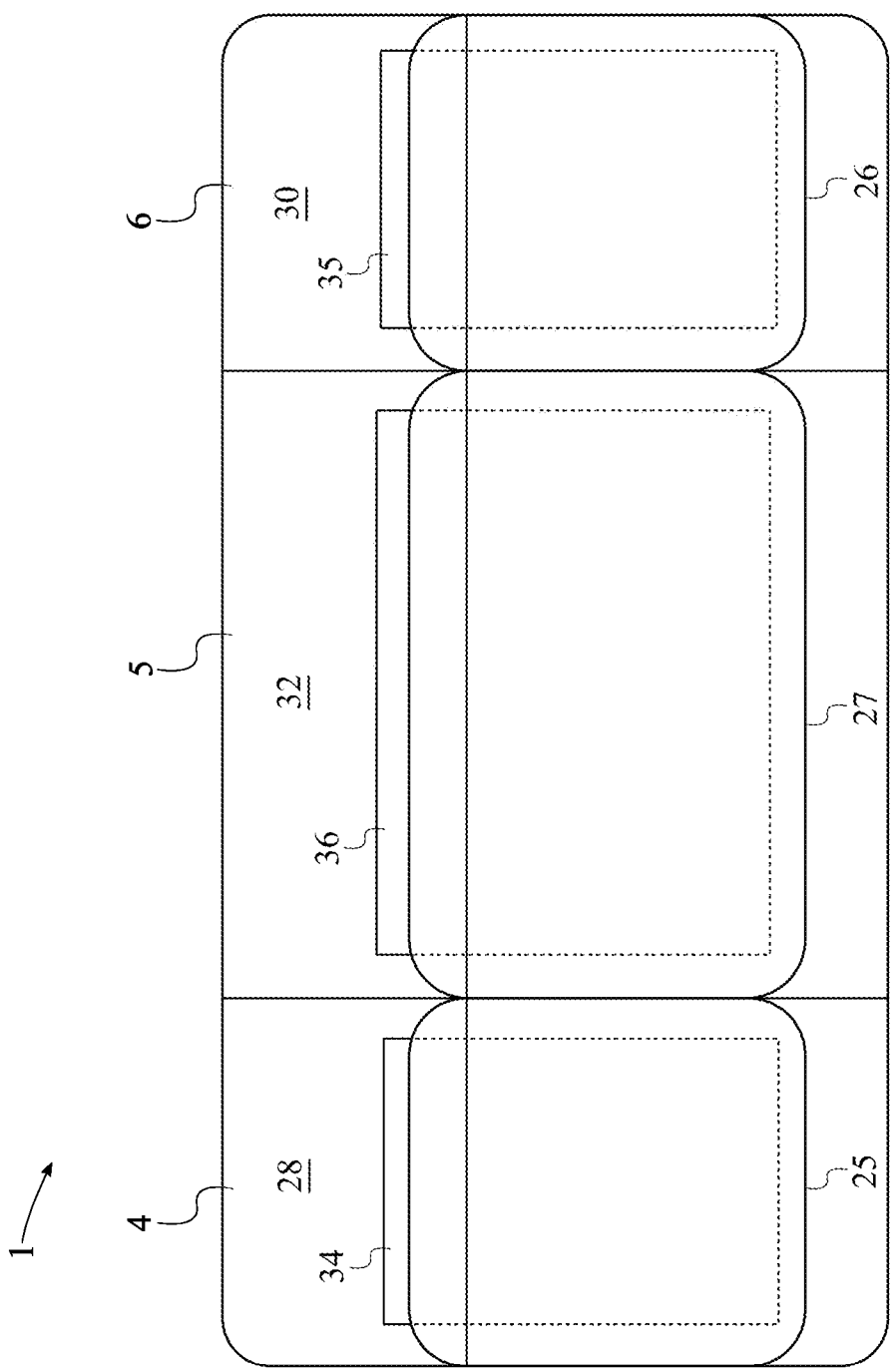
FIG. 7 is a schematic diagram displaying the therapeutic devices within the pockets.

With reference to FIG. 3, the present invention may further comprise a left pocket 25, a right pocket 26, and a middle pocket 27. The left pocket 25, the right pocket 26, and the middle pocket 27 provide storage area that allows a user to carry small items within the present invention. The left section 4, the right section 6, and the middle each further comprises a front face 28, 30, 32 and a rear face 29, 31, 33. The front face 28, 30, 32 is the area which contacts the head of the user when present invention is worn. The left pocket 25 is mounted onto the front face 28 of the left section 4, the right pocket 26 is mounted to the front face 30 of the right section 6, and the right pocket 26 is mounted to the front face 32 of the middle section 5. This arrangement allows the user to easily store small items within the present invention. With reference to FIG. 7 and further, the present invention may further comprise at least one left therapeutic device 34, at least one right therapeutic device 35, and at least one middle therapeutic device 36. The at least one left therapeutic device 34, the at least one right therapeutic device 35, and the at least one middle therapeutic device 36 can be any type of device that provides therapeutic benefits such as, but not limited to, a heating or cooling pack. Moreover, the at least one middle therapeutic device 36 may preferably a heating device that is powered and control through universal serial bus (USB) technology. In this case, the middle pocket 27 includes a cutout which allows a user to run a USB cable to the at least one middle therapeutic device 36. The at least one left therapeutic device 34 is positioned within the left pocket 25, the at least one right therapeutic device 35 is positioned within the right pocket 26, and the at least one middle therapeutic device 36 is positioned within the middle pocket 27. The arrangement allows the present invention, when worn, to effectively provide therapeutic benefits to the user through the at least one left therapeutic device 34, the at least one right therapeutic device 35, and the at least one middle therapeutic device 36.

Figure 8:
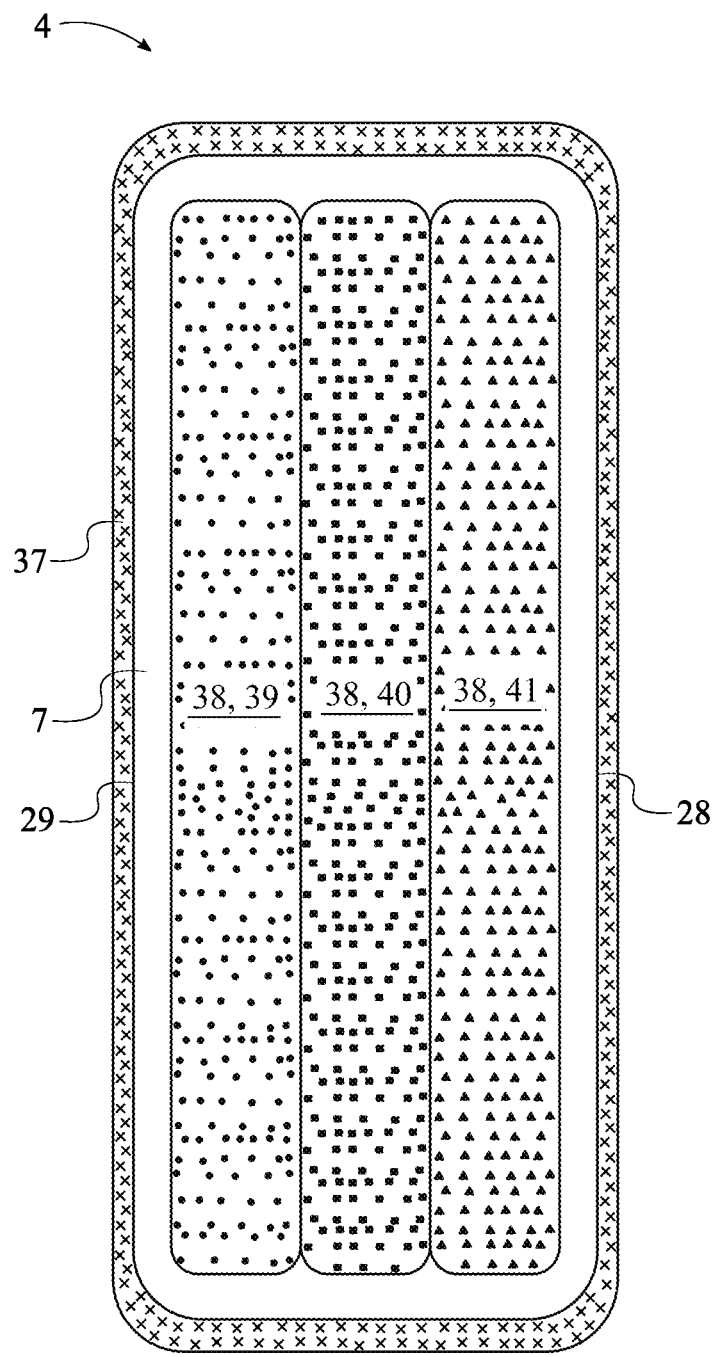
FIG. 8 is a schematic cross-sectional diagram displaying the plurality of fillings of the left section.
Figure 9:
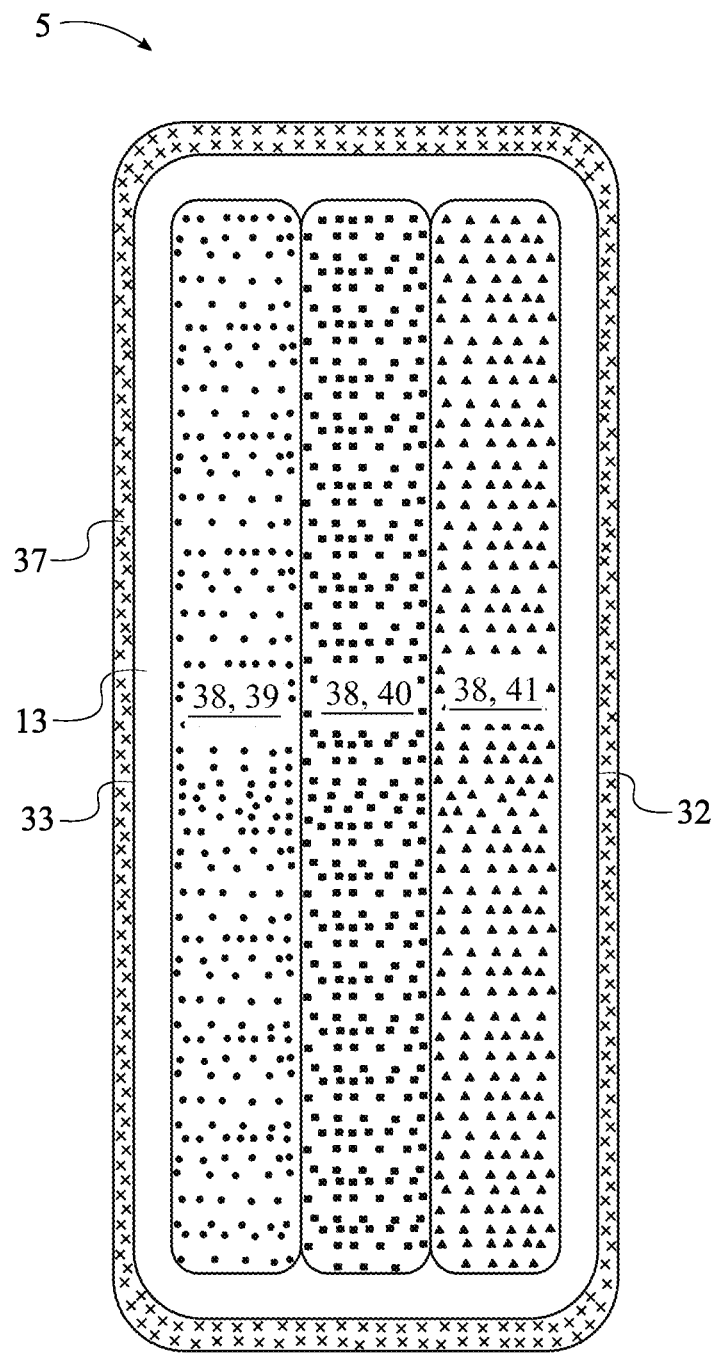
FIG. 9 is a schematic cross-sectional diagram displaying the plurality of fillings of the middle section.
Figure 10:
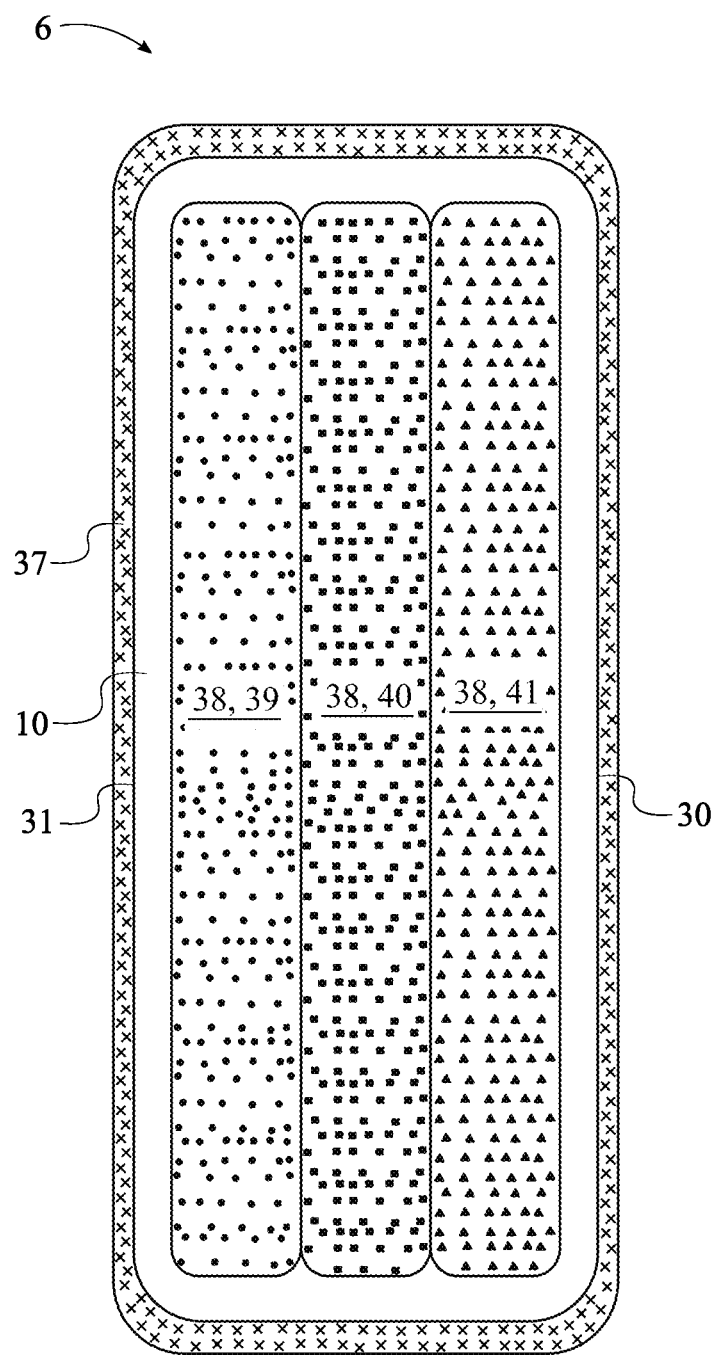
FIG. 10 is a schematic cross-sectional diagram displaying the plurality of fillings of the right section.

With reference to FIGS. 8 through 10, the left section 4, the middle section 5, and the right section 6 each further comprises a padding 37 and a plurality of fillings 38. The padding 37 provides a soft and comfortable surface area to the pillow body 1. The plurality of fillings 38 provides cushion, weight, and heat-conducting properties to the pillow body 1. The plurality of fillings 38 is layered upon each other within the section body. This arrangement provides cushioned support to the pillow body 1. The section body 7, 10, 13 is enclosed by the padding 37 in order to provide a soft and comfortable surface for the head of the user when the present invention is worn. Further and in the preferred embodiment of the present invention, the plurality of fillings 38 comprises a pillow filling 39, a foam filling 40, and a weighted heat-sink filling 41. The pillow filling 39 is preferably material that is used to fill standard pillows. The foam filling 40 can be any type of foam material that provides cushion and support. The weighted heat-sink filling 41 is preferably flax seeds but may be any other material such as polypropylene pellets. Flax seeds or polypropylene pellets provide weight and heat-conducting properties to the pillow body 1. Further, the weighted heat-sink filling 41 the user to microwave the present invention which can warm the present invention. The weighted heat-sink filling 41 is positioned adjacent to the front face 28, 30, 32. This arrangement allows the user to experience the heat-conducting effects provided by the weighted heat-sink filling 41 when the present invention is worn. The pillow filling 39 is positioned adjacent to the rear face 29, 31, 33. This arrangement provides cushion for the head of the user when the present invention is worn. Further, the foam filling 40 is positioned in between the weighted heat-sink filling 41 and the pillow filling 39. This arrangement provides more cushion, but also provides support for the head of the user when the present invention is worn.

Figure 4:
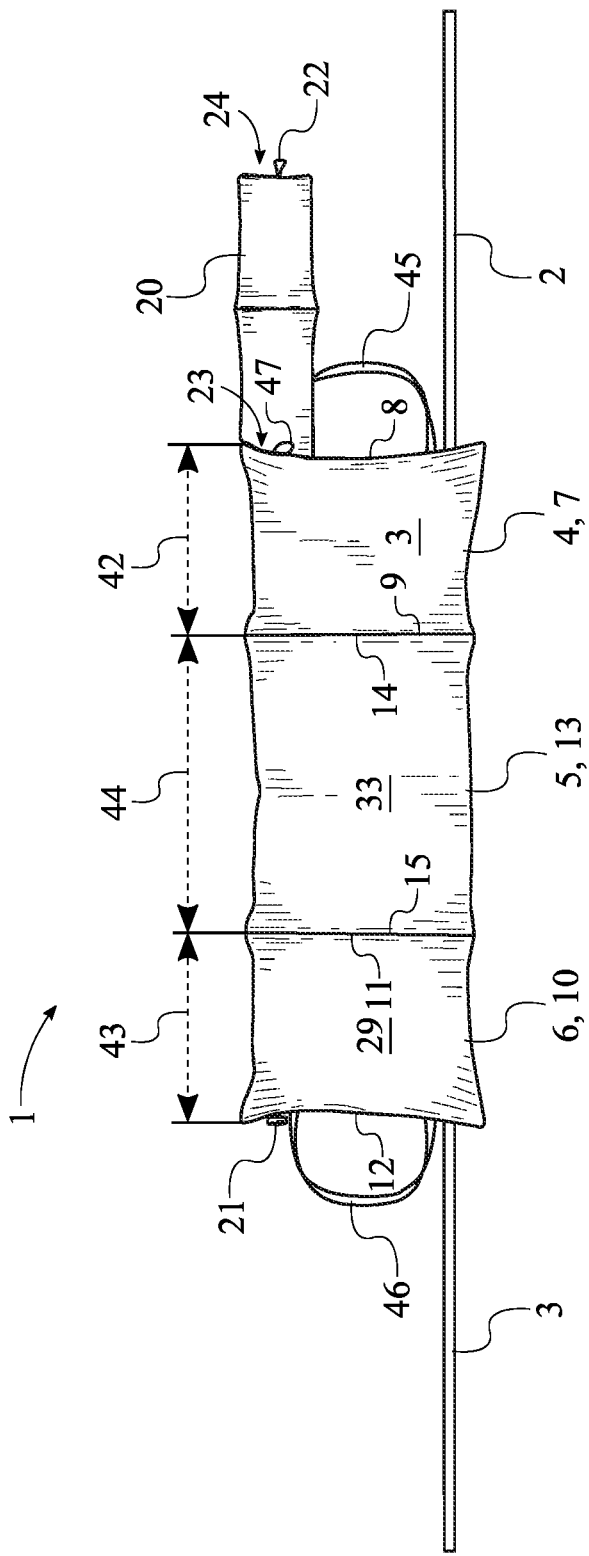
FIG. 4 is a rear view of the present invention in the open configuration.

With reference to FIGS. 3 and 4, the left section 4, the right section 6, and the middle section 5 each includes a section width 42, 43, 44 that traverses from the first edge 8, 11, 14 to the second edge 9, 12, 15. A ratio between the section width 42 of the left section 4 and the section width 44 of the middle section 5 is 1:2. A ratio between the section width 43 of the right section 6 and the section width 44 of the middle section 5 is 1:2. A ratio between the section width 42 of the left section 4 and the section width 43 of the right section 6 is 1:1. In further detail, the section width 44 of the middle section is preferably twice as large than the section width 42 of the left section 4 and the section width 43 of the right section 6. Further, the section width 44 of the middle section 5 is preferably larger to properly support the back of the head of the user. The left section 4 and the right section 6 are primarily used to cover the sides of the head of the user.

With reference to FIG. 1, the present invention may further comprise a first handle 45 and a second handle 46. In the closed configuration for travel, the first handle 45 and the second handle 46 are gripping elements used to carry the present invention. Further and in the closed configuration when the user is wearing the present invention, the first handle 45 and the second handle 46 can be used to apply pressure to the shoulders and neck of the user in order to relieve tension. The first handle 45 is connected adjacent to the first edge 8 of the left section 4 and is positioned offset from the fixed end 16 of the left strap 2. This arrangement positions the first handle 45 in order to be easily grasped by the user. Similarly, the second handle 46 is connected adjacent to the second edge 12 of the right section 6 and is positioned offset from the fixed end 18 of the right strap 3. This arrangement positions the second handle 46 in order to be easily grasped by the user.

In another embodiment of the present invention and with reference to FIGS. 2 and 4, the present invention may further comprise a pillow loop 47. The pillow loop 47 is connected adjacent to the first edge 8 of the left section 4. This arrangement positions the pillow loop 47 in order to be easily accessed by the user. Further, the pillow loop 47 is positioned adjacent to the eye-mask 20. Moreover, the pillow loop 47 allows the pillow body 1 to be fully secured into the closed configuration. In further detail, the pillow loop 47 can be engaged to the eye-mask hook 21 in order for the pillow body 1 to be secured into the closed configuration.

Although the invention has been explained in relation to its preferred embodiment, it is to be understood that many other possible modifications and variations can be made without departing from the spirit and scope of the invention as hereinafter claimed.

What is claimed is:
1. A travel spa pillow comprises:
a pillow body;
a left strap;
a right strap;
the pillow body comprising a left section, a middle section and a right section;
the left section, the middle section and the right section each comprising a section body, a first edge and a second edge;
the left strap and the right strap each comprising a fixed end and a free end;
the first edge and the second edge being positioned parallel to each other;
the first edge and the second edge being positioned opposite to each other across the section body;
the second edge of the left section being foldably connected along of the first edge of the middle section;
the second edge of the middle section being foldably connected along of the first edge of the right section;
the fixed end of the left strap being connected adjacent to the first edge of the left section;
the fixed end of the right strap being connected adjacent to the second edge of the right section;
a left pocket;
a right pocket;
a middle pocket;
the left section, the right section and the middle section each further comprising a front face and a rear face;
the left pocket being mounted onto the front face of the left section;
the right pocket being mounted onto the front face of the right section;
the middle pocket being mounted onto the front face of the middle section;
at least one left therapeutic device;
the at least one left therapeutic device being positioned within the left pocket;
at least one right therapeutic device;
the at least one right therapeutic device being positioned within the right pocket;
at least one middle therapeutic device;
the at least one middle therapeutic device being positioned within the middle pocket;
the at least one left therapeutic device, the at least one right therapeutic device and the at least one middle therapeutic device each being powered and controlled through universal serial bus (USB) technology; and
the left pocket, the right pocket and the middle pocket each comprising a cutout for receiving a USB cable.

2. The travel spa pillow as claimed in claim 1 comprises:
wherein the pillow body is in an open configuration; and
the first edge of the left section being positioned offset from the second edge of the right section.

3. The travel spa pillow as claimed in claim 1 comprises:
wherein the pillow body is in a closed configuration;
the first edge of the left section being positioned adjacent to the second edge of the right section; and
the free end of the left strap being attached to the free end of the second tie strap.

4. The travel spa pillow as claimed in claim 1 comprises:
an eye-mask;
an eye-mask hook;
an eye-mask loop;
the eye-mask comprises a first mask end and a second mask end;
the first mask end being hingedly connected to the first edge of the left section;
the first mask end being positioned offset from the fixed end of the left strap;
the eye-mask loop being connected adjacent to the second mask end; and
the eye-mask hook being connected onto the second edge of the right section.

5. The travel spa pillow as claimed in claim 1 comprises:
the left section, the middle section, and the right section each further comprises a padding and a plurality of fillings;
the plurality of fillings being layered upon each other within the section body; and
the section body being enclosed by the padding.

6. The travel spa pillow as claimed in claim 5 comprises:
the left section, the right section, and the middle section each further comprises a front face and a rear face;
the plurality of fillings comprises a pillow filling, a foam filling, and a weighted heat-sink filling;
the weighted heat-sink filling being positioned adjacent to the front face;
the pillow filling being positioned adjacent to the rear face; and
the foam filling being positioned in between the weighed heat-sink filling and the pillow filling.

7. The travel spa pillow as claimed in claim 1 comprises:
the left section, the middle section, and the right section each further comprises a section width, the section width traversing from the first edge to the second edge;
a ratio between the section width of the left section and the section width of the middle section being 1:2;
a ratio between the section width of the right section and the section width of the middle section being 1:2; and
a ratio between the section width of the left section and the section width of the right section being 1:1.

8. The travel spa pillow as claimed in claim 1 comprises:
a first handle;
the first handle being connected adjacent to the first edge of the left section; and the first handle being positioned offset from the fixed end of the left strap.

9. The travel spa pillow as claimed in claim 1 comprises:

a second handle;

the second handle being connected adjacent to the second edge of the right section; and the second handle being positioned offset from the fixed end of the right strap.

10. The travel spa pillow as claimed in claim 1 comprises:

a pillow loop; and the pillow loop being connected adjacent to the first edge of the left section.

\* \* \* \* \*